(12) United States Patent
Himes et al.

(10) Patent No.: US 7,654,160 B2
(45) Date of Patent: Feb. 2, 2010

(54) SAMPLING PROBE ENABLING THE MEASUREMENT OF GASEOUS SPECIES IN PARTICLE-LADEN FLUE GAS

(75) Inventors: Richard Himes, Dove Canyon, CA (US); John Pisano, Moreno Valley, CA (US); Matthew R. Smith, North Lake, IL (US)

(73) Assignee: Electric Power Research Institute, Inc., Charlotte, NC (US)

( * ) Notice: Subject to any disclaimer, the term of this patent is extended or adjusted under 35 U.S.C. 154(b) by 433 days.

(21) Appl. No.: 11/613,304

(22) Filed: Dec. 20, 2006

(65) Prior Publication Data

US 2008/0148871 A1 Jun. 26, 2008

(51) Int. Cl.
G01N 1/22 (2006.01)

(52) U.S. Cl. .................. 73/863.61; 73/863.51
(58) Field of Classification Search .................. 73/23.2, 73/863.31, 863.33, 863.43, 863.51, 863.58, 73/863.81, 863.61, 864.73
See application file for complete search history.

(56) References Cited

U.S. PATENT DOCUMENTS

| | | | | |
|---|---|---|---|---|
| 3,382,721 A | * | 5/1968 | Tinkham et al. | 73/864.73 |
| 3,473,388 A | * | 10/1969 | Lynn | 73/863.58 X |
| 3,803,921 A | * | 4/1974 | Dieterich | 73/863.61 X |
| 4,215,565 A | * | 8/1980 | Zanker | 73/863.61 X |
| 4,353,260 A | * | 10/1982 | Round | 73/863.61 X |
| 4,481,833 A | * | 11/1984 | Bajek | 73/863.81 X |
| 4,703,661 A | * | 11/1987 | Evers | 73/861.66 |

OTHER PUBLICATIONS

Drawing showing use of shields which reduces the measurement path length but do not influence the particle loading over the actual measurement path, 1 page, "published" by May 2007.

* cited by examiner

Primary Examiner—Thomas P Noland
(74) Attorney, Agent, or Firm—Trego, Hines & Ladenheim, PLLC

(57) ABSTRACT

A sampling probe for enabling the analysis of gaseous species in a particle-laden flue gas. The sampling probe includes a tube for being inserted into a fluid stream of a particle-laden flue gas substantially perpendicular thereto to cause the fluid stream to separate and flow around the tube. The tube includes a first opening extending along a first axially extending face of the tube downstream relative to the fluid stream such that a portion of the gas enters the tube through the first opening for analysis within the tube, and a second opening extending along a second axially extending face of the tube such that the gas that enters the tube through the first opening exits the tube after analysis into the fluid stream through the second opening to allow analysis of the gas.

4 Claims, 5 Drawing Sheets

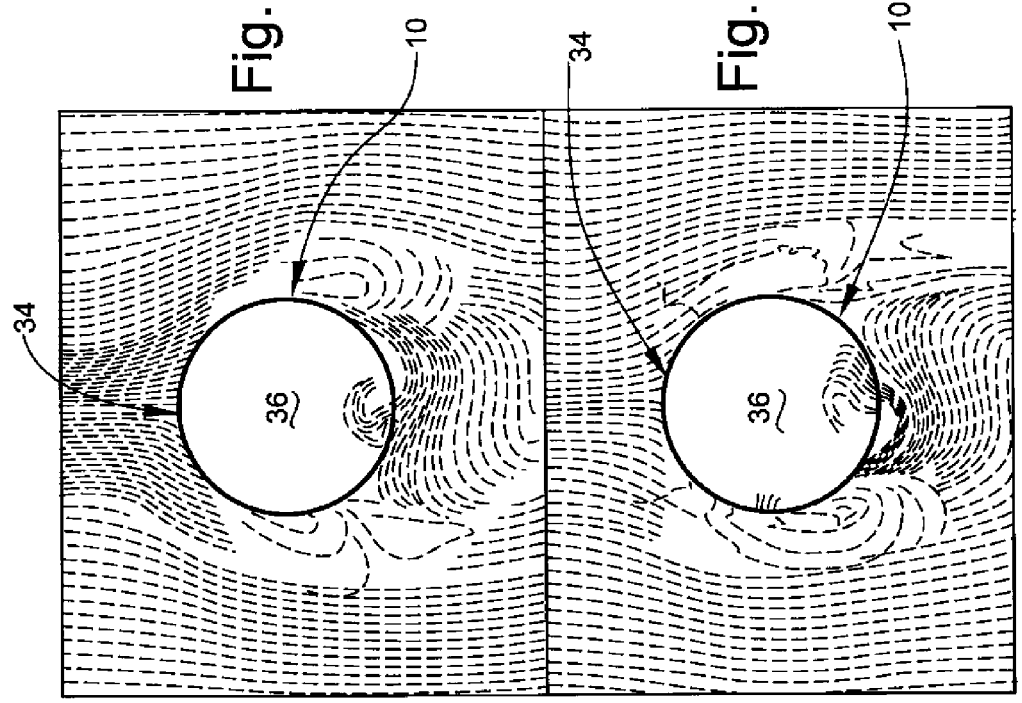
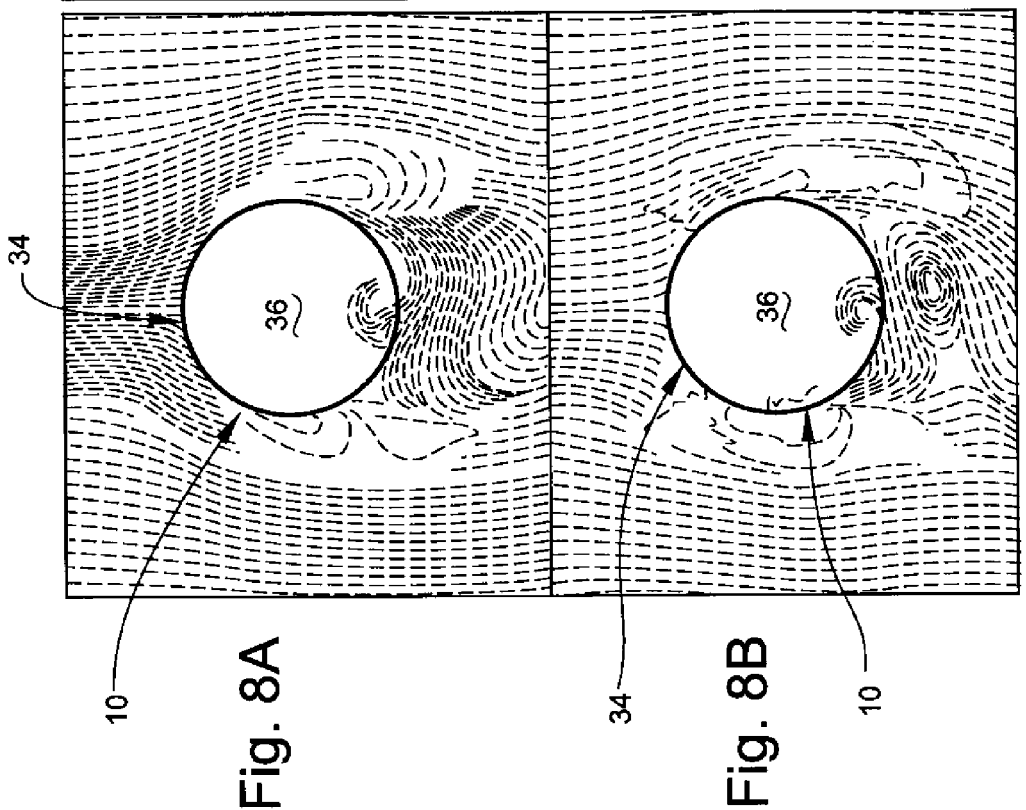

SAMPLING PROBE ENABLING THE MEASUREMENT OF GASEOUS SPECIES IN PARTICLE-LADEN FLUE GAS

TECHNICAL FIELD AND BACKGROUND OF THE INVENTION

The present invention relates to the field of gas analysis. In particular, the invention relates to a sampling probe that enables the measurement of gaseous species in a particle-laden flue gas.

The continuous measurement of gaseous species in fossil fuel fired boilers is beneficial to the timely control of the combustion process, as well as ancillary pollution reduction technologies. Typically, optical measurement techniques are employed when conducting measurements of gaseous species. However, combustion of fuels containing ash, such as coal, results in particle-laden flue gas that scatters transmitted energy from an optical measurement device, thereby minimizing the potential measurement distance. In many applications, such as in ductwork on coal-fired utility boilers with dimensions greater than 15 feet, the utilization of optical measurement techniques and devices becomes impractical.

Accordingly, there is a need for a sampling probe that minimizes the influence of ash particles on optical measurement devices, and enables the measurement of gaseous species over an extended path length using optical measurement techniques.

SUMMARY OF THE INVENTION

Therefore it is an object of the invention to provide a sampling probe that may be inserted into a flue gas section of a boiler.

It is another object of the invention to provide a sampling probe that allows flue gas to enter an interior volume of the sampling probe while minimizing the number of particles entering.

It is another object of the invention to provide a sampling probe that allows the use of optical measurement techniques to measure/analyze the gaseous species of the flue gas over extended path lengths.

These and other objects of the present invention are achieved in the preferred embodiments disclosed below by providing a sampling probe for analyzing a gas in a fluid stream including a tube for being inserted into the fluid stream substantially perpendicular thereto to cause the fluid stream to separate and flow around the tube. The tube includes a first opening extending along a first axially extending face of the tube downstream relative to the fluid stream such that a portion of the gas enters the tube through the first opening for analysis within the tube, and a second opening extending along a second axially extending face of the tube such that the gas that enters the tube through the first opening exits the tube after analysis into the fluid stream through the second opening.

According to another preferred embodiment of the invention, the sampling probe further includes a third opening extending along a third axially extending face of the tube and aligned with the second opening to allow gas that enters the tube through the first opening to exit into the fluid stream through the third opening.

According to another preferred embodiment of the invention, the third opening is positioned on the third axially extending face in a staggered relation to the second opening on the second axially extending face.

According to another preferred embodiment of the invention, the sampling probe further includes a fourth opening extending along the first axially extending face and substantially parallel to the first opening to allow gas to enter the tube.

According to another preferred embodiment of the invention, the first opening and the fourth opening are positioned on the first axially extending face in staggered relation to each other.

According to another preferred embodiment of the invention, a sampling probe for analyzing a gas in a fluid stream includes a first row of slots extending along a first axially extending face of the sampling probe, a second row of slots extending along a second axially extending face of the sampling probe and substantially perpendicular to the first row of slots, and a third row of slots extending along a third axially extending face of the sampling probe and substantially perpendicular to the first row of slots and diametrically aligned with the second row of slots. The first, second, and third rows of slots are positioned such that when the sampling probe is positioned in the fluid stream, the gas strikes an axially extending face of the sampling probe opposite the first row of slots. This causes particles in the gas to be separated from the gas and a portion of the gas to enter the sampling probe through the first row of slots for analysis.

According to another preferred embodiment of the invention, the second and third rows of slots are arranged to allow the gas to exit the sampling probe and into the fluid stream.

According to another preferred embodiment of the invention, the sampling probe further includes a fourth row of slots extending along the first axially extending face and substantially parallel to the first row of slots to allow gas to enter the sampling probe.

According to another preferred embodiment of the invention, the first row of slots and fourth row of slots are staggered in relation to each other.

According to another preferred embodiment of the invention, the second row of slots and the third row of slots are staggered in relation to each other.

According to another preferred embodiment of the invention, the slots in the first row are separated by a distance substantially equal to a length of a respective slot in the first row.

According to another preferred embodiment of the invention, at least one end of the sampling probe extends through an opening in a wall of the duct to position the sampling probe transverse to the fluid stream.

According to another preferred embodiment of the invention, the sampling system further includes optics mounted external to the duct to allow an optical beam to analyze the gas entering the sampling probe.

According to another preferred embodiment of the invention, the sampling system further including supports for supporting the sampling probe within the duct such that deflection in the sampling probe is minimized.

According to another preferred embodiment of the invention, a method of analyzing a fluid stream of gas includes the steps of providing a tube having a first opening extending along a first axially extending face and a second opening extending along a second axially extending face; positioning the tube in the fluid stream; and allowing the gas to enter the tube through the first opening and exit the tube through the second opening. The method further includes the step of analyzing the gas in the tube.

According to another preferred embodiment of the invention, the method further includes the step of orienting the tube in the fluid stream such that the first opening is positioned downstream of the fluid stream.

According to another preferred embodiment of the invention, the method further includes the step of supporting the tube to prevent the tube from bending.

According to another preferred embodiment of the invention, the method further includes the step of positioning an optical measurement device in cooperation with the tube such that the gas entering the tube is analyzed by the optical measurement device.

BRIEF DESCRIPTION OF THE DRAWINGS

The invention may be best understood by reference to the following description in conjunction with the accompanying drawing figures in which:

FIGS. 8A-8D show flow streamlines of the flue gas around the sampling probe of FIG. 1.

DESCRIPTION OF THE PREFERRED EMBODIMENT AND BEST MODE

Figure 1:
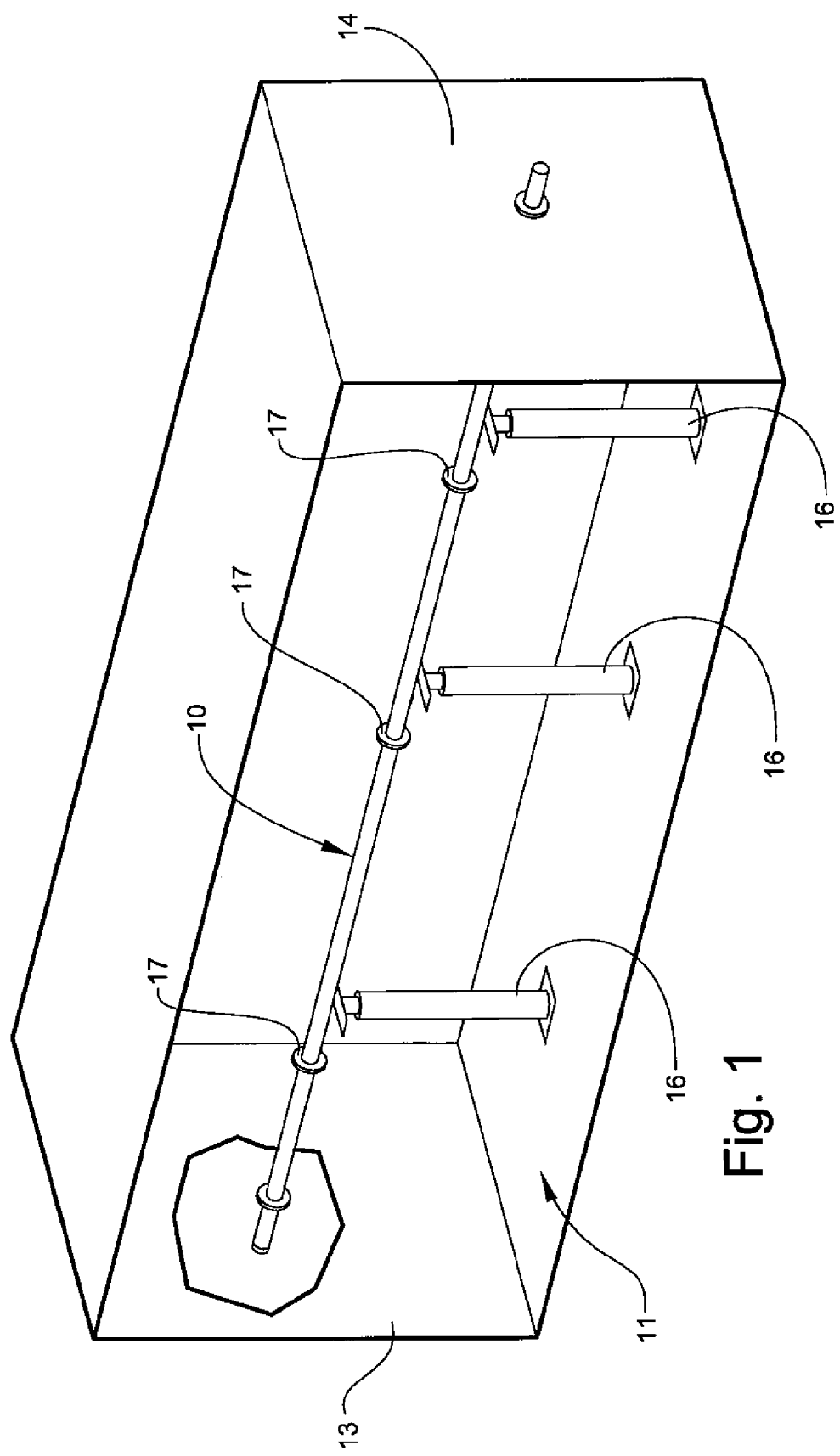
FIG. 1 shows a sampling probe according to an embodiment of the invention installed in a duct of a boiler.
Figure 2:
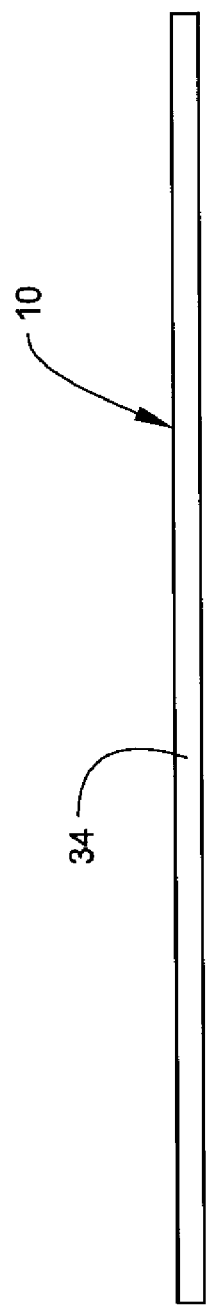
FIG. 2 is a top view of the sampling probe of FIG. 1.

Referring now specifically to the drawings, a sampling probe according to an embodiment of the invention is illustrated in FIG. 1 and shown generally at reference numeral 10. The sampling probe 10 is positioned in a flue gas duct 11 of a boiler system (not shown) to allow measurement and/or analysis of the gaseous species passing therethrough. The sampling probe 10 extends through side walls 13 and 14 of the duct 11 and is supported by stands 16 to prevent bending in the sampling probe 10. It should be appreciated that the sampling probe 10 may be supported by any suitable means to prevent bending, such as suspending the sampling probe 10 with cable-like structures connected to slip rings 17 positioned on the sampling probe 10, or welding a stand to the sampling probe 10 at desired intervals.

Referring to FIGS. 2-5, the sampling probe 10 is preferably tubular and includes a plurality of openings or slots formed in a wall of the sampling probe 10 at predetermined positions. As shown in FIG. 6, two rows of slots 22 and 23 are cut into a bottom 24 of the sampling probe 10 at about the six o'clock position, one row of slots 27 is cut into a left side 28 of the sampling probe 10 at about a nine o'clock position, and one row of slots 30 is cut into a right side 31 of the sampling probe 10 at about a three o'clock position. It will be appreciated that the use of the terms top, bottom, left side, and right side are not meant to limit the shape or orientation of the sampling probe 10, and are only used for purposes of illustration.

Figure 3:
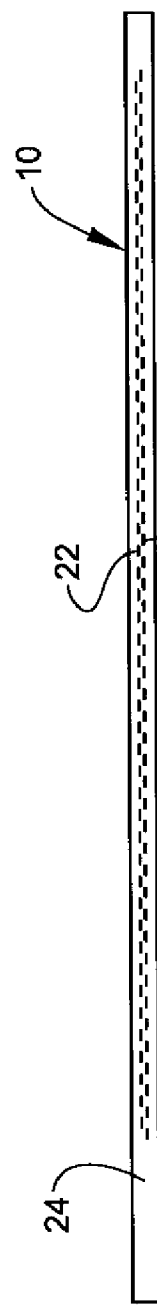
FIG. 3 is a bottom view of the sampling probe of FIG. 1.
Figure 4:
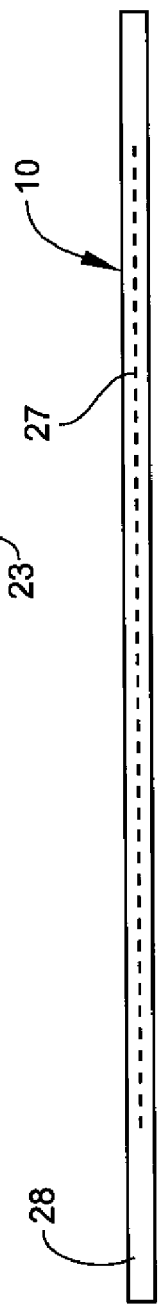
FIG. 4 is a left side view of the sampling probe of FIG. 1.
Figure 5:
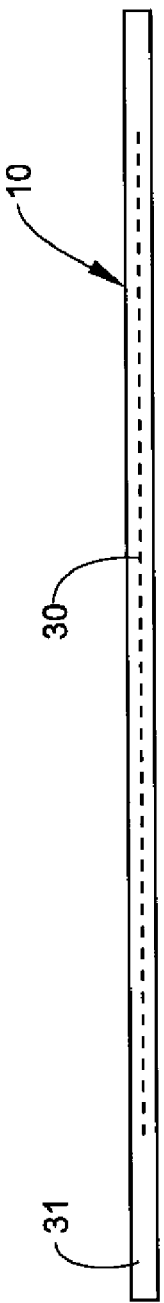
FIG. 5 is a right side view of the sampling probe of FIG. 1.
Figure 6:
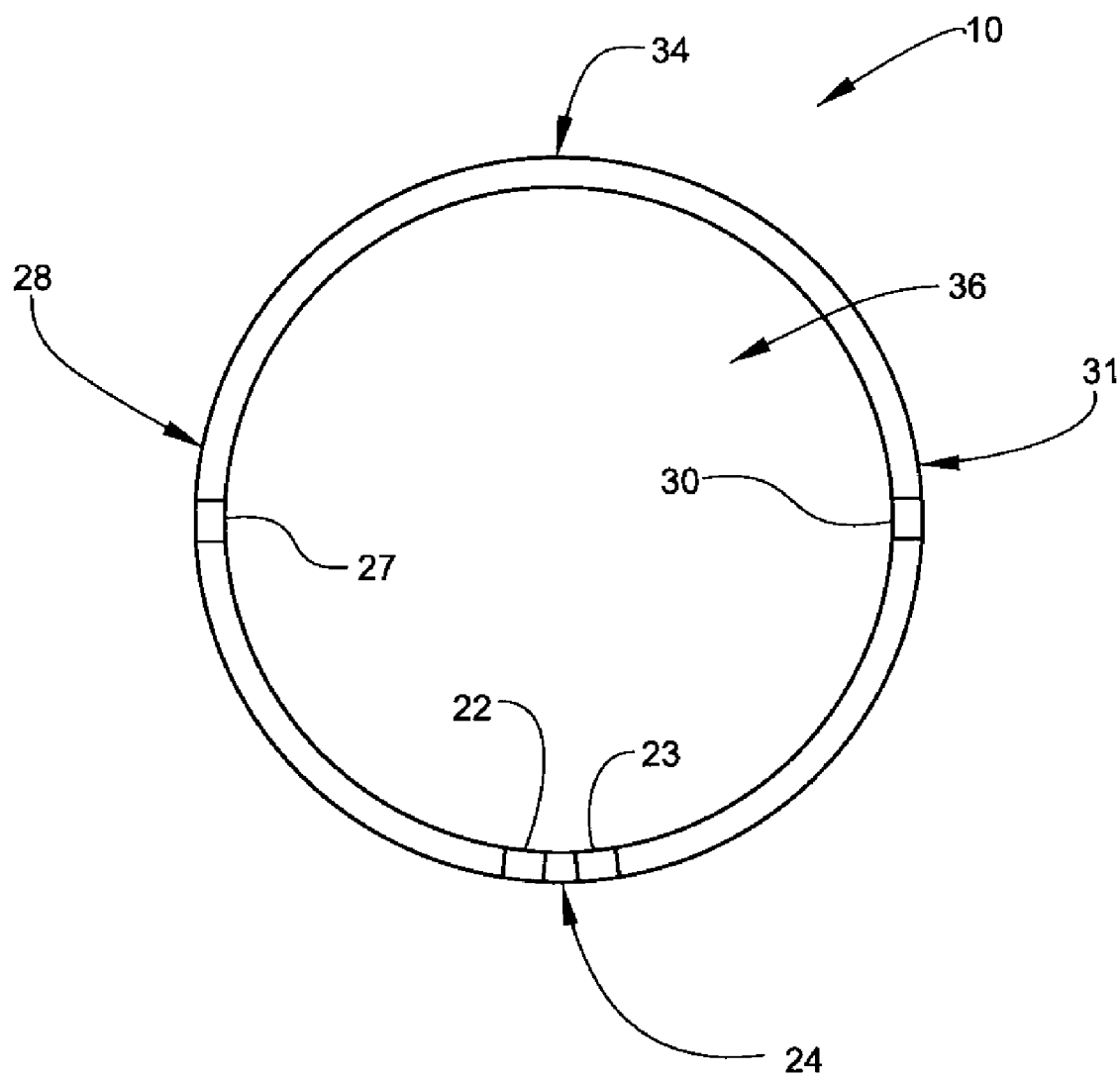
FIG. 6 is a cross-section of the sampling probe of FIG. 1.
Figure 7:
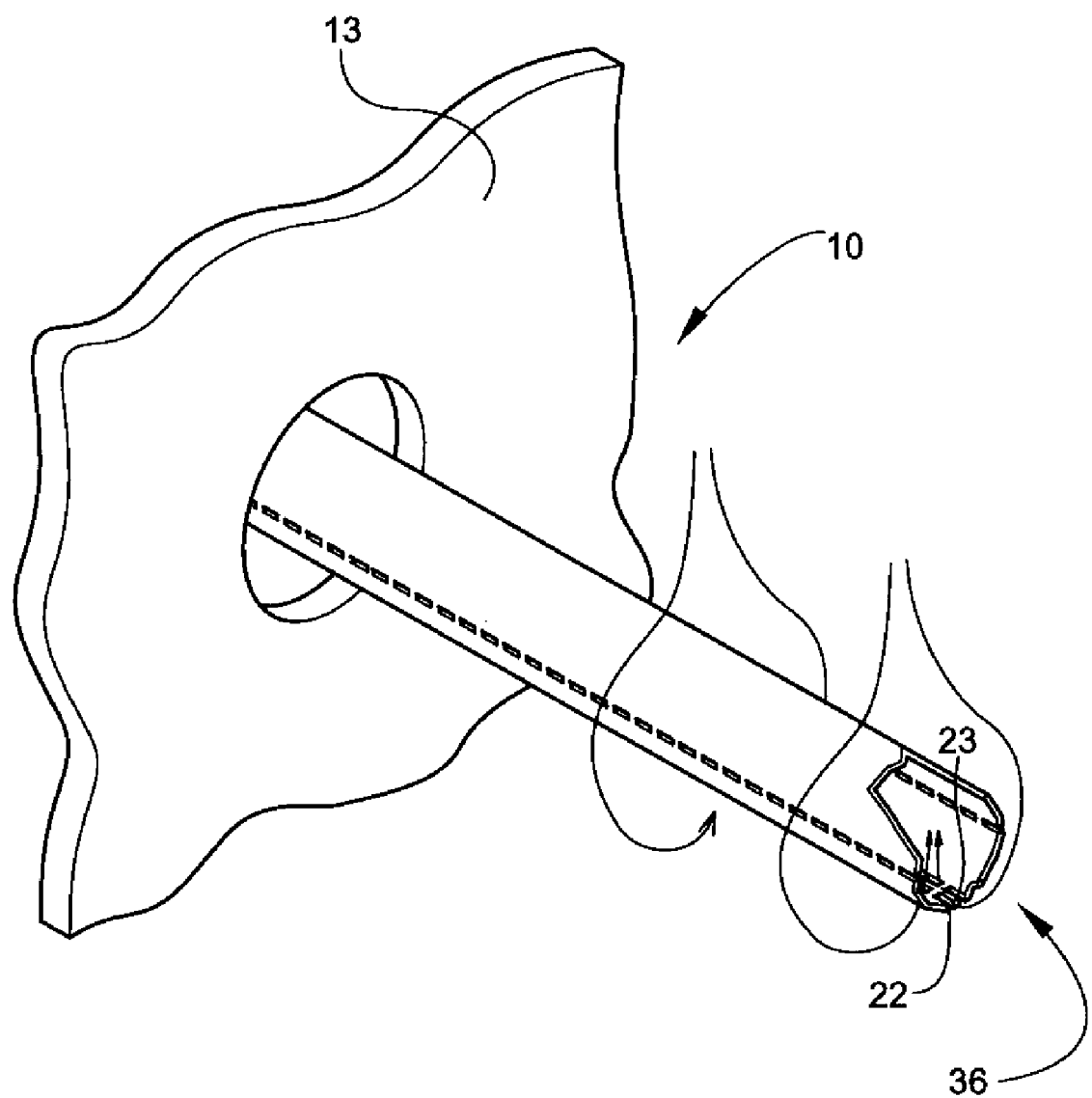
FIG. 7 shows the orientation of the sampling probe of FIG. 1 with respect to flue gas flow.

As shown in FIGS. 4 and 5, the row of slots 27 and row of slots 30 are linear, positioned on opposing sides 28 and 31 of the sampling probe 10, and are positioned such that the slots 27 are staggered with respect to the slots 30. Each of the slots 27 are separated by a distance equivalent to the length of each of the slots 27, and each of the slots 30 are separated by a distance equivalent to the length of each of the slots 30. As shown in FIG. 3, the slots 22 and 23 are staggered along the bottom 24 of the sampling probe 10. Each of the rows of slots 22 and 23 extend the entire length of the probe 10 as it resides in the duct 11.

Referring to FIGS. 7 and 8A-8D, the sampling probe 10 is positioned in the duct 11 such that the sampling probe 10 is transverse to the flow of flue gas in the duct 11, and is oriented such that a top 34 of the sampling probe 10 is angled toward the flow of the flue gas. As shown in FIGS. 8A-8D, the streamlines associated with the flow (from top to bottom) are separated around the circumference of the sampling probe 10, creating a recirculation eddy on the bottom 24 of the sampling probe 10 due to the formation of a low pressure zone.

Flue gas is continuously induced into an interior volume 36 of the sampling probe 10 through the slots 22 and 23 and then passed through slots 27 and slots 30 along opposing sides 28 and 31 of the sampling probe 10 back into the flue gas flow around the sampling probe 10. The high velocity flow along the outside surface of the sampling probe 10, in combination with the separated flow, creates a high velocity and low pressure zone that pulls flue gas out of the sampling probe 10. This flow of flue gas in the sampling probe 10 is then traversed with an optical beam of a known type for measurement and/or analysis of gaseous species of interest.

Particles, such as fly ash, in the flue gas are separated aerodynamically, with large particles not being able to turn 180 degrees, thereby becoming separated from the gas streamlines entering into the sampling probe 10. Since particles are separated from the gas streamlines entering the sampling probe 10, the obscuration of an optical measurement beam caused by particles in the measurement volume is minimized. This is shown in Table 1 below.

TABLE 1

| Probe Used | Fly Ash (g/Nm$^3$) | Path (m) | I return (mW) | I return (%) | I return (%-m) |
| --- | --- | --- | --- | --- | --- |
| No | 10.6 | 5 | 0.002 | 0.03 | 0.15 |
| Yes | 10.6 | 19.5 | 0.3 | 3.75 | 73.1 |

As shown in Table 1, the laser return power of an optical measurement device is approximately 150 times greater when the sampling probe 10 is used, despite the fact that the path length is four times greater than the path length without the sampling probe 10. Further tests across the sampling probe 10 demonstrated measurement capability in excess of 64 feet with limited power attenuation.

The sampling probe 10 also minimizes deflection due to mechanical or thermal stress, thereby maintaining optical alignments and enabling either monostatic or bistatic measurements. The sampling probe 10 provides optical alignment for a monostatic or bistatic arrangement of optics. It may be used in a cross-duct configuration with optics mounted external to the duct, or used in a single port access configuration with high temperature optics used to reflect an optical beam in a monostatic arrangement.

A sampling probe is described above. Various details of the invention may be changed without departing from its scope. Furthermore, the foregoing description of the preferred embodiments of the invention and best mode for practicing the invention are provided for the purpose of illustration only and not for the purpose of limitation.

We claim:

1. A sampling probe for analyzing a gas in a fluid stream, comprising:
    (a) a tube for being inserted into the fluid stream substantially perpendicular thereto to cause the fluid stream to separate and flow around the tube;
    (b) a first opening extending along a first axially extending face of the tube downstream relative to the fluid stream such that a portion of the gas enters the tube through the first opening for analysis within the tube;
    (c) a second opening extending along a second axially extending face of the tube such that the gas that enters the tube through the first opening exits the tube after analysis into the fluid stream through the second opening; and
    (d) a third opening extending along a third axially extending face of the tube and aligned with the second opening to allow gas that enters the tube through the first opening to exit into the fluid stream through the third opening.

2. The sampling probe according to claim 1, wherein the third opening is positioned on the third axially extending face in a staggered relation to the second opening on the second axially extending face.

3. The sampling probe according to claim 1, and further including a fourth opening extending along the first axially extending face and substantially parallel to the first opening to allow gas to enter the tube.

4. The sampling probe according to claim 3, wherein the first opening and the fourth opening are positioned on the first axially extending face in staggered relation to each other.

* * * * *